US010251618B2

(12) United States Patent
Lee et al.

(10) Patent No.: US 10,251,618 B2
(45) Date of Patent: Apr. 9, 2019

(54) DIGITAL MAMMOGRAPHY DEVICE WITH PRESSURE PAD PRESSURE CONTROL

(71) Applicant: GENERAL ELECTRIC COMPANY, Schenectady, NY (US)

(72) Inventors: Chang Hwa Lee, Gyeonggi-do (KR); Tae Woo Nam, Gyeonggi-do (KR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 684 days.

(21) Appl. No.: 14/775,169

(22) PCT Filed: Mar. 12, 2014

(86) PCT No.: PCT/KR2014/002053
§ 371 (c)(1),
(2) Date: Jul. 21, 2016

(87) PCT Pub. No.: WO2014/142544
PCT Pub. Date: Sep. 18, 2014

(65) Prior Publication Data
US 2016/0367206 A1  Dec. 22, 2016

(30) Foreign Application Priority Data
Mar. 12, 2013 (KR) .................. 10-2013-0026175

(51) Int. Cl.
*A61B 6/00* (2006.01)
*A61B 6/04* (2006.01)

(52) U.S. Cl.
CPC ............. *A61B 6/502* (2013.01); *A61B 6/04* (2013.01); *A61B 6/0414* (2013.01); *A61B 6/4233* (2013.01); *A61B 6/4441* (2013.01)

(58) Field of Classification Search
CPC ....... A61B 6/04; A61B 6/0407; A61B 6/0414; A61B 6/0421; A61B 6/0457; A61B 6/4441; A61B 6/502
(Continued)

(56) References Cited

U.S. PATENT DOCUMENTS

| 6,574,499 B1 * | 6/2003 | Dines ............... A61B 6/0414 128/915 |
| 6,882,700 B2 * | 4/2005 | Wang ................. A61B 6/025 378/197 |

(Continued)

FOREIGN PATENT DOCUMENTS

| CN | 202665563 U | 1/2013 |
| CN | 105726049 A | 7/2016 |

(Continued)

OTHER PUBLICATIONS

European Search Report and Written Opinion issued in connection with corresponding EP Application No. 14763661.7-1666 dated Sep. 30, 2016.

(Continued)

*Primary Examiner* — Allen C. Ho

(57) ABSTRACT

Disclosed herein is a digital mammography device. The digital mammography device comprises a pressure pad configured to be movably installed between an X-ray generator for irradiating X-rays and a detector for receiving X-rays that have passed through an object to be imaged, in such a way as to apply pressure to the object to be imaged; a pressure pad driving part configured to include a motor and a power transferring part for moving the pressure pad by means of the power of the motor, and an applied pressure transferring part configured to include a coupling block to which the pressure pad is fixed to the power transferring part and relatively and movably connected to the coupling block, (Continued)

and provides an electrical signal depending on a relative movement displacement between the coupling block and the mobile block.

7 Claims, 5 Drawing Sheets

(58) Field of Classification Search
USPC .............................. 378/37, 209, 208; 5/601
See application file for complete search history.

(56) References Cited

U.S. PATENT DOCUMENTS

| | | | |
|---|---|---|---|
| 7,003,073 B2 | 2/2006 | Andreasson et al. | |
| 7,092,482 B2 * | 8/2006 | Besson | A61B 6/0414 378/37 |
| 7,327,826 B2 * | 2/2008 | Hanke | A61B 6/06 378/155 |
| 7,418,081 B2 * | 8/2008 | Holler | A61B 6/4233 378/37 |
| 7,443,949 B2 * | 10/2008 | Defreitas | 378/208 |
| 7,443,950 B2 * | 10/2008 | Sendai | A61B 6/0414 378/195 |
| 7,453,979 B2 * | 11/2008 | Sendai | A61B 6/025 378/23 |
| 7,453,982 B1 * | 11/2008 | Klausz | A61B 6/4441 378/197 |
| 7,545,908 B2 * | 6/2009 | Hemmendorff | A61B 6/502 378/205 |
| 7,566,172 B2 * | 7/2009 | Kashiwagi | A61B 6/06 378/155 |
| 7,573,977 B2 * | 8/2009 | Tsujita | A61B 6/502 378/197 |
| 7,613,276 B2 * | 11/2009 | Sendai | A61B 6/0414 378/37 |
| 7,639,778 B2 * | 12/2009 | Kashiwagi | A61B 6/0414 378/180 |
| 7,732,775 B2 * | 6/2010 | Kashiwagi | A61B 5/103 250/363.05 |
| 7,742,559 B2 * | 6/2010 | Iordache | A61B 5/6843 378/195 |
| 7,746,975 B2 * | 6/2010 | Kashiwagi | A61B 6/5241 378/37 |
| 7,756,245 B2 * | 7/2010 | Kanemitsu | A61B 6/04 378/208 |
| 7,756,246 B2 * | 7/2010 | Mikami | A61B 6/0414 378/37 |
| 7,778,388 B2 * | 8/2010 | Sendai | A61B 6/025 378/22 |
| 7,809,111 B2 * | 10/2010 | Meer | A61B 6/502 378/114 |
| 7,869,563 B2 * | 1/2011 | Defreitas | A61B 6/107 378/37 |
| 7,940,890 B1 * | 5/2011 | Linev | A61B 6/06 378/146 |
| 8,475,376 B2 * | 7/2013 | Mikami | A61B 6/0414 600/407 |
| 8,594,275 B2 * | 11/2013 | Matsuura | A61B 6/0414 378/208 |
| 8,787,522 B2 * | 7/2014 | Smith | A61B 6/025 378/37 |
| 8,792,617 B2 * | 7/2014 | Baetz | A61B 6/4035 378/16 |
| 9,060,739 B2 | 6/2015 | Kim | |
| 9,282,942 B2 * | 3/2016 | Mertelmeier | A61B 6/502 |
| 9,314,213 B2 * | 4/2016 | Takata | A61B 6/0414 |
| 9,332,947 B2 * | 5/2016 | DeFreitas | A61B 6/04 |
| 9,339,244 B2 * | 5/2016 | Takata | A61B 6/544 |
| 9,451,923 B2 * | 9/2016 | Hemmendorff | A61B 6/4452 |
| 9,468,411 B2 * | 10/2016 | Muller | A61B 6/025 |
| 9,517,038 B2 * | 12/2016 | Williams | A61B 6/0414 |
| 9,597,040 B2 * | 3/2017 | Hemmendorff | A61B 6/025 |
| 9,636,073 B2 * | 5/2017 | Evans | A61B 6/502 |
| 10,010,304 B2 * | 7/2018 | Morita | A61B 6/0414 |
| 2008/0080668 A1 | 4/2008 | Kashiwagi | |
| 2012/0020464 A1 | 1/2012 | Matsuura | |
| 2012/0328074 A1 | 12/2012 | Souchay et al. | |
| 2013/0016807 A1 | 1/2013 | Kallert et al. | |

FOREIGN PATENT DOCUMENTS

| | | |
|---|---|---|
| DE | 3227258 A1 | 2/1984 |
| FR | 2681521 A1 | 3/1993 |
| JP | 2003310594 A | 11/2003 |
| JP | 2010110571 A | 5/2010 |
| JP | 2010179030 A | 8/2010 |
| KR | 20120087751 A | 8/2012 |

OTHER PUBLICATIONS

Notice of Allowance issued in connection with corresponding KR Application No. 10-2013-0026175 dated May 28, 2014.
International Search Report and Written Opinion issued in connection with corresponding PCT Application No. PCT/KR2014/002053 dated May 30, 2014.
Machine Translation and Office Action issued in connection with corresponding CN Application No. 201480027128.5 dated Jun. 30, 2017.

* cited by examiner

DIGITAL MAMMOGRAPHY DEVICE WITH PRESSURE PAD PRESSURE CONTROL

Embodiments of the present invention relates to a digital mammography device photographing a breast using X-ray, and more particularly, to a digital mammography device capable of monitoring and adjusting strength of force applied to the breast of the patient from a pressure pad.

BACKGROUND

X-ray is generally defined as an electromagnetic wave having a short wavelength corresponding to wavelengths of 0.01 nm to 10 nm, and an X-ray photographing is referred to as a radiography that transparently displays an inside of a photographing target by the high penetrable X-rays.

As well known, the X-ray involves an attenuation phenomenon depending on a material, a density, and a thickness of an object such as Compton scattering, a photoelectric effect, or the like during a process in which the X-ray penetrates through the object. Therefore, the X-ray photographing projects and displays the inside of the photographing target on a plane based on an amount of attenuation of the X-ray accumulated during the process in which the X-ray penetrates through the photographing target, and to this end, a dedicated X-ray system is used.

Recently, an X-ray imaging technology has rapidly evolved to a digital X-ray imaging technology having various advantages such as relatively high resolution, a wide dynamic region, an easy generation of an electrical signal, simple data process and storage, and the like, instead of a conventional analog scheme using a film while being grafted to a semiconductor field. A digital based imaging technology meets the clinical and environmental requirements of an early diagnosis of diseases based on excellent diagnostic ability of a digital image.

Therefore, "digital mammography", which is a breast dedicated X-ray photographing technology capable of detecting a lesion and a micro-calcification for detection and early diagnosis of a breast cancer by expressing an internal structure of the breast in a high resolution image utilizing unique contrast ability of biological tissues of the X-ray has been proposed. The above-mentioned digital mammography has rapidly propagated due to unique characteristics such as an image expansion, a reduction in the number of photographs, an increase in resolution, and minimization of exposure through an adjustment of brightness and contrast ratio, together with various advantages of the digital X-ray imaging technology.

A general mammography device includes a column of a column shape which is perpendicular to a bottom; a C-arm that generally shows a C letter or a shape similar to the C letter at both end portions which are bent in arc shapes facing each other in a state in which a middle portion is connected so as to be elevatable and rotatable along the column; an X-ray generator mounted in one end portion of the C-arm to irradiate X-ray toward the other end portion facing one end portion; a detector mounted in the other end portion of the C-arm to face the X-ray generator; and a pressure pad performing a straight-line reciprocating motion between the X-ray generator and the detector along an internal surface of the C-arm.

In the mammography device as described above, when a patient enters a photographing position, the C-arm is elevated and rotated along the column to adjust a height and an angle so that the breast of the patient is placed at a target position on the detector, and when the pressure pad is moved in a direction of the detector to pressurize the breast, the X-ray is irradiated from the X-ray generator and is received at the detector. The detector generates an electrical signal for each position which is proportional to an incident amount of X-ray, and when the electrical signal and position information are read and are processed by an image processing algorithm, an X-ray image of the breast for the corresponding angle may be obtained. If necessary, the above-mentioned process may be repeated while the X-ray generator and the detector are rotated to face each other while having the breast therebetween, and as a result, the mammography device may obtain high resolution images for the breast of the patient at various angles.

In the general mammography device showing the above-mentioned photographing principle, a key driving mechanism for minimizing inconvenience of the patient and obtaining a high quality X-ray image is a pressure operation of the pressure pad. That is, since the pressure pad directly applies pressure to the breast during the X-ray photographing, it is directly related to pain or inconvenience which is felt by the patient. According to the related art, when the pressure pad pressurizes the breast placed on an inspection plate, more pressure than necessary may be applied, and as a result, there is a possibility that the patient undergoes more pain than necessary. Particularly, since sizes, densities, and the like of the breast of the patients are different from each other, suitable pressure should be applied accordingly, but there is a problem that the suitable pressure is not accurately and reliably controlled. An improvement method capable of increasing reliability for the pressure operation of the pressure pad and precisely and accurately controlling the pressure operation is required.

BRIEF SUMMARY OF THE INVENTION

An embodiment of the present invention is relates to a digital mammography device capable of performing a control so that suitable pressure is applied using a monitored electrical signal while monitoring pressure applied to a patient through a pressure pad in real time, and protecting the patient by interrupting driving force of the pressure pad in the case in which excessive pressure is applied.

In another embodiment of the present invention, the digital mammography device is configured to transfer force using a mechanical mechanism including a spring between the pressure pad and a pressure pad driving part. In this manner, the device may reduce a risk that the excessive pressure is suddenly applied to a body of the patient even in the case in which a malfunction due to error of an electronic control device occurs.

According to an exemplary embodiment of the present invention, there is provided a digital mammography device including: a pressure pad configured to be movably installed between an X-ray generator irradiating X-ray and a detector receiving the X-ray penetrating through a subject and compress the subject; a pressure pad driving part configured to include a motor and a power transferring part moving the pressure pad using power of the motor; and an applied pressure transferring part configured to include a coupling block to which the pressure pad is fixed and a moving block fixed to the power transferring part and relatively and movably connected to the coupling block, and provide an electrical signal depending on a relative movement displacement between the coupling block and the moving block.

The applied pressure transferring part may include: a spring disposed between the coupling block and the moving block and deformed depending on the relative movement displacement; and a load cell disposed at one end portion of the spring to provide the electrical signal according to a deformation of the spring. The digital mammography device may further include: a piston member configured to be installed between one end portion of the spring and the load cell.

The digital mammography device may further include: a controller configured to control the motor with the electrical signal and may further include: a safety switch configured to control the motor when the relative movement displacement exceeds a preset range regardless of whether or not the controller is functional.

The digital mammography device according to an embodiment of the present invention may perform the control so that suitable pressure is applied using the monitored electrical signal while monitoring the pressure applied to the patient through the pressure pad in real time, and may protect the patient by interrupting the driving force of the pressure pad in the case in which excessive pressure is applied.

In addition, the digital mammography device according to an embodiment of the present invention may prevent the risk that excessive pressure is suddenly applied to the body of the patient even in the case in which the malfunction due to the error of the electronic control device occurs, by transferring the force using the mechanical mechanism including the spring between the pressure pad and the pressure pad driving part.

DETAILED DESCRIPTION

Figure 1:
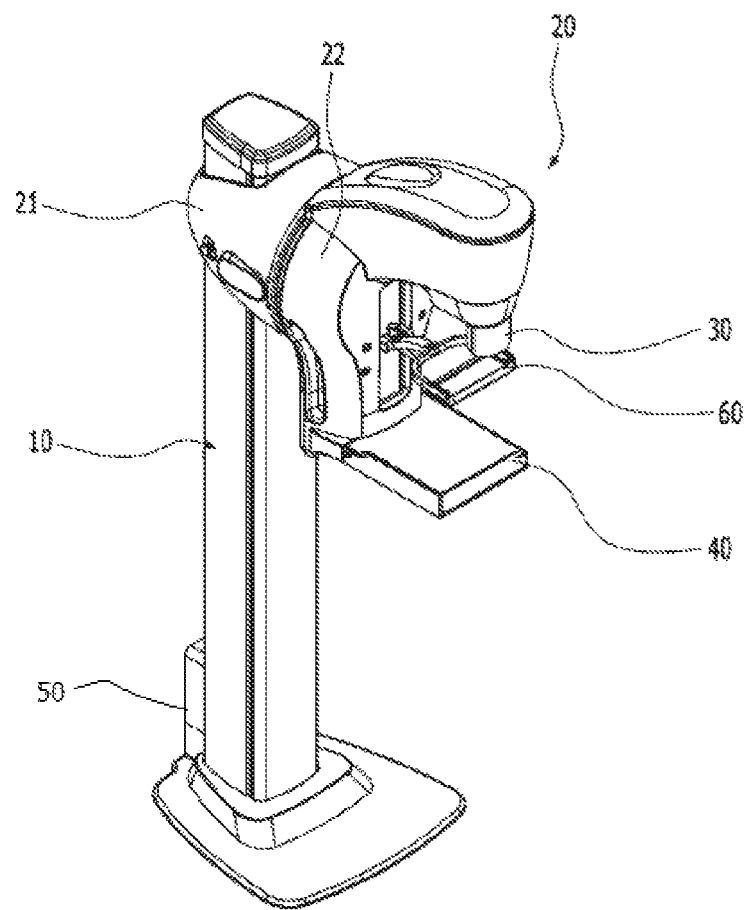
FIG. 1 is a perspective view showing a mammography device according to an exemplary embodiment of the present invention.

Hereinafter, exemplary embodiments of the present invention will be described with reference to the accompanying drawings. A scope of the present invention may be clearly understood through the exemplary embodiments. However, the present invention is not limited to the exemplary embodiments described below and may be modified in various forms within the scope to which the present invention pertains. Meanwhile, like reference numerals used in several drawings denote a component having the same characteristics, and a description of the component having the same reference numeral as the component described with reference to any one drawing may be omitted from the description of another drawing.

Figure 2:
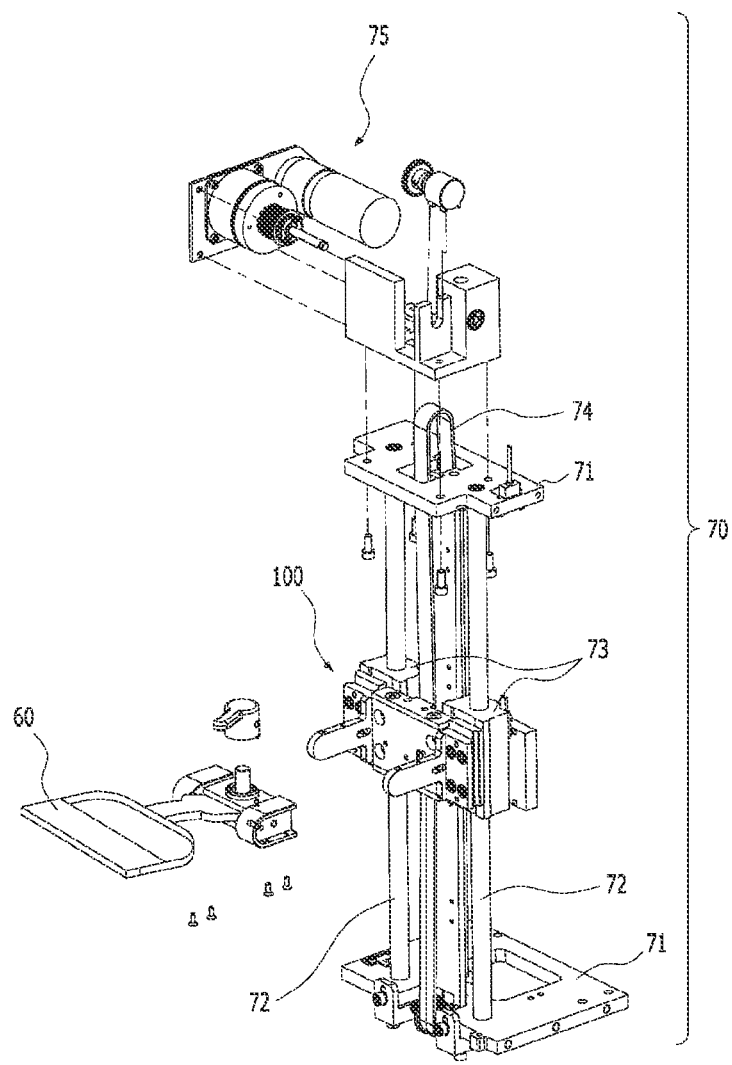
FIG. 2 is a partial exploded perspective view showing configurations of a pressure pad driving part and an applied pressure transferring part in the digital mammography device according to an exemplary embodiment of the present invention.

FIG. 1 is a perspective view showing a mammography device according to an exemplary embodiment of the present invention and FIG. 2 is a partial exploded perspective view showing configurations of a pressure pad driving part and an applied pressure transferring part in the digital mammography device according to an exemplary embodiment of the present invention.

The digital mammography device according to an embodiment of the present invention includes a column 10 which stands to be perpendicular to a ground and supports a load of the device; a C type arm 20 that generally shows a C letter or a shape similar to the C letter by both end portions which are bent in arc shapes facing each other in a state in which a middle portion is connected so as to be elevatable and rotatable along the column 10; an X-ray generator 30 mounted in one end portion of the C type arm 20 to irradiate X-ray toward the other end portion facing one end portion; a detector 40 mounted in the other end portion of the C type arm 20 to face the X-ray generator 30; a pressure pad 60 performing a straight-line reciprocating motion between the X-ray generator 30 and the detector 40; a pressure pad driving part 70 driving the pressure pad 60; and an applied pressure transferring part 100 installed between the pressure pad 60 and the pressure pad driving part 70, transferring applied pressure from the power transferring part of the pressure pad driving part 70 to the pressure pad 60, and measuring the transferred applied pressure to provide an electrical signal.

The column 10 has a column shape which is perpendicular to a bottom, and an extension part 21 extended from the middle portion of the C type arm 20 is elevatably coupled to the column 10. A vertical connection part 22 connecting one end portion and the other end portion facing each other of the C type arm 20 is rotatably coupled to the extension part 21.

The X-ray generator 30 collides electrons having high kinetic energy with a metal target to generate X-ray, and more particularly includes a collimator that controls an irradiation direction and an irradiation area of the X-ray, or the like.

The detector 40 is a device that receives the X-ray penetrating through a subject, that is, penetrating through a breast of a patient to generate an electrical signal accordingly, and according to an exemplary embodiment of the present invention, a general technique such as a direct transforming scheme that directly obtains the electrical signal from the X-ray without a separate intermediate operation according to an X-ray transforming scheme, an indirect transforming scheme that transforms the X-ray into visible ray and indirectly obtains the electrical signal by the visual ray, or the like may be widely used.

The pressure pad 60 pressurizes the breast on a support fixture which is separately installed at a front side of the detector 40 or the support fixture including the detector 40 to the support fixture side, and the breast in the pressurized state is photographed using the X-ray generator 30 and the detector 40. The pressure pad driving part 70 is configured to vertically move the pressure pad 60 and provide applied pressure, and may be installed at the vertical connection part 22 of the C type arm 20.

The applied pressure transferring part 100 transfers a motion and force generated by the pressure pad driving part 70 to the pressure pad 60, measures applied pressure applied to the breast of the patient, that is, a strength of repulsive force transferred to the pressure pad 60 from the breast of the patient, and generates the electrical signal using the measured strength of repulsive force, such that a controller 50 may control an operation of the pressure pad driving part 70 based on the electrical signal. For example, the strength of the applied pressure itself or a change trench thereof may be detected in order to be used to generate a control signal driving a motor of the pressure pad driving part 70. If the strength of the applied pressure exceeds a preset value, it is also possible to interrupt power of the pressure pad driving part 70, drive the pressure pad driving part 70 in an opposite direction, or the like.

The pressure pad driving part 70 includes a motor which is electrically controlled, and a power transferring part transforming power of the motor into a vertical reciprocal movement form. The power transferring part may include a gear box and a pulley which are connected to the motor, a belt wound around the pulley to be rotated, and the like.

The exemplary embodiment shown in FIG. 2 will be described in more detail. The pressure pad driving part 70 includes a pair of horizontal brackets 71; a pair of guide shafts 72 which are perpendicular to the horizontal brackets 71 and installed so as to be in parallel to each other; a guide block 73 of which a movement is guided by the pair of guide shafts 72 and to which a component of the applied pressure transferring part 100 is coupled; a belt 74 moving the guide block 73 and the applied pressure transferring part 100; and a driving motor and a gear box 75 driving the belt 74.

Figure 3:
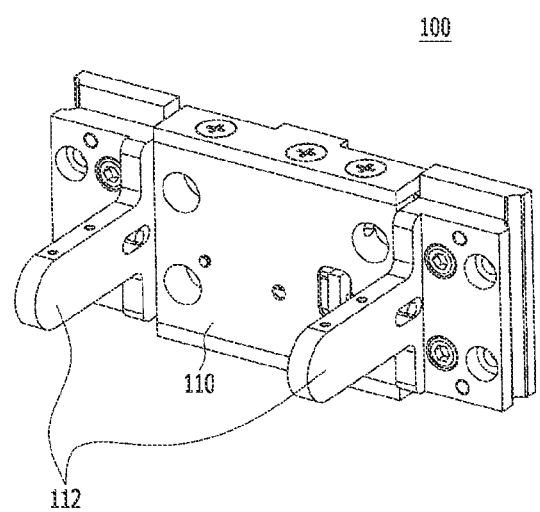
FIG. 3 is a front perspective view showing the applied pressure transferring part of the digital mammography device according to an exemplary embodiment of the present invention.
Figure 4:
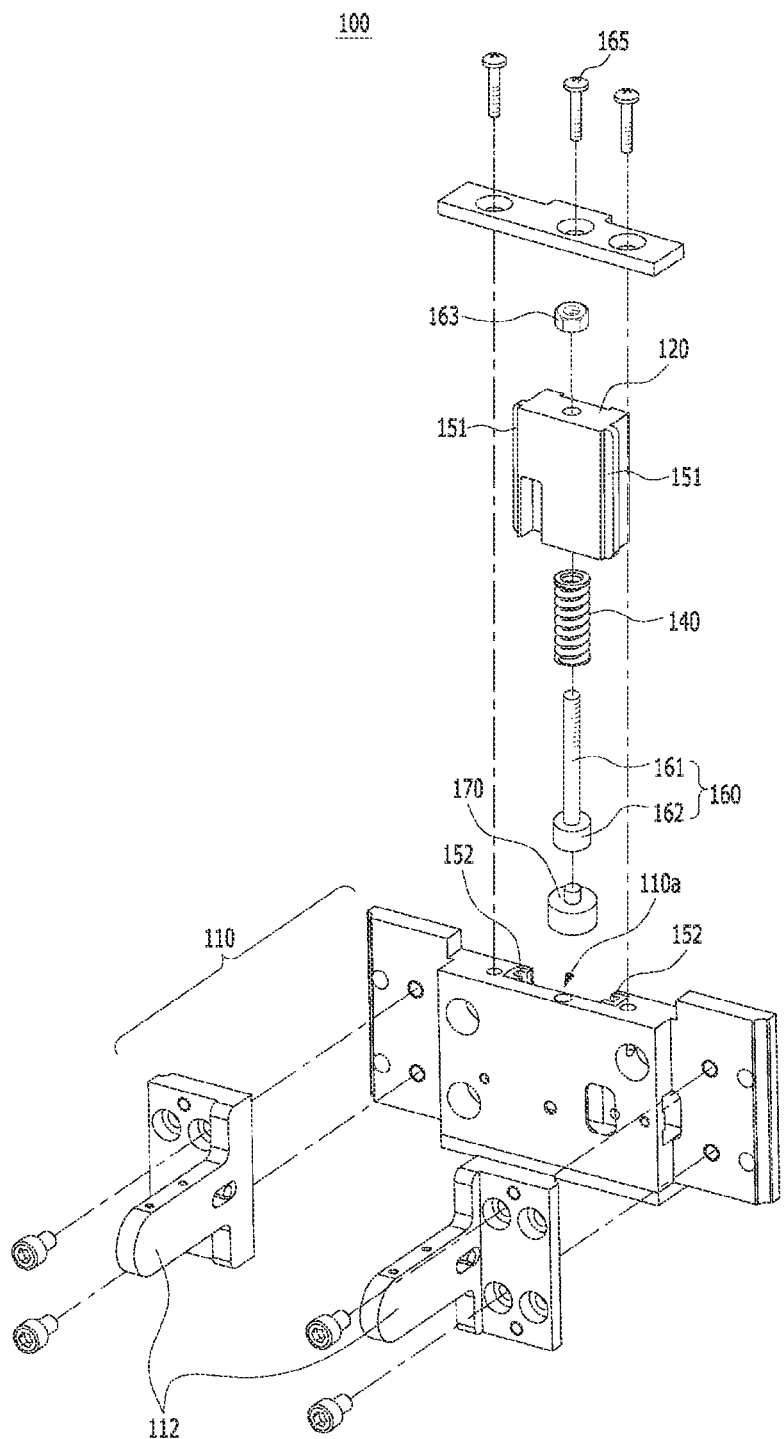
FIG. 4 is an exploded perspective view showing a configuration of the applied pressure transferring part in the digital mammography device according to an exemplary embodiment of the present invention.

FIG. 3 is a front perspective view showing the applied pressure transferring part of the digital mammography device according to an exemplary embodiment of the present invention and FIG. 4 is an exploded perspective view showing a configuration of the applied pressure transferring part in the digital mammography device according to an exemplary embodiment of the present invention.

The applied pressure transferring part 100 includes a moving block 120 fixed to the belt 74, which is a member substantially performing a vertical reciprocal motion as a part of the power transferring part; and a coupling block 110 having the moving block 120 which is coupled to one side thereof to be relatively movable and the pressure pad 60 fixed to the other side thereof. The coupling block 110 is installed with guide rails 152 and guide protrusions 151 are formed on sides of the moving block 120 corresponding to the guide rails 152, such that a relative movement of the coupling block 110 and the moving block 120 may be guided. In addition, the coupling block 110 is provided with pressure pad coupling parts 112, to which the pressure pad 60 is fastened.

A spring 140 deformed depending on a relative movement displacement between the coupling block 110 and the moving block 120 and transferring force; and a load cell 170 disposed at one end portion of the spring 140 and measuring a strength of force transferred through the spring 140 to provide the electrical signal may be included between the coupling block 110 and the moving block 120. In addition, a piston member 160 transferring all of the force across the spring 140 to a measuring part of the load cell 170 may be further included between the spring 140 and the load cell 170.

The piston member 160 may include a piston body 162 which is directly in contact with the spring 140 and the load cell 170, and a piston rod 161 extended from the piston body 162 into the spring 140 to hold a position of the spring 140.

Figure 5:
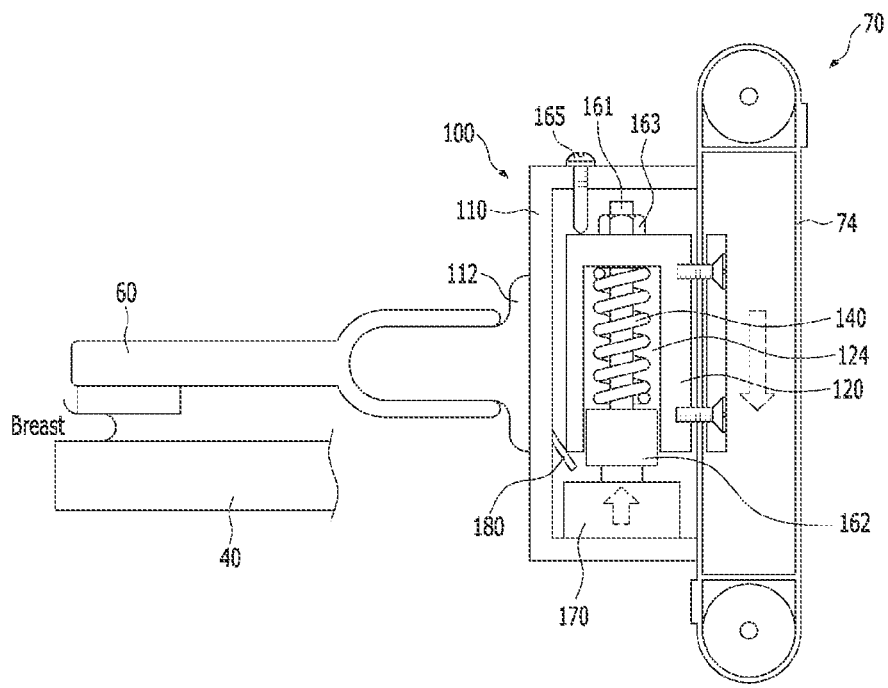
FIG. 5 is a schematic diagram showing the configuration of the applied pressure transferring part in the digital mammography device according to an exemplary embodiment of the present invention.

FIG. 5 is a schematic diagram showing the configuration of the applied pressure transferring part in the digital mammography device according to an exemplary embodiment of the present invention.

The spring 140 may be installed in a spring housing part 124 provided in the moving block 120, for example. An operation range of the spring 140 may be limited by the piston member 160 described above. For example, an initial state of the spring 140 may be adjusted by allowing the piston rod 161 to penetrate through an upper end portion of the spring housing part 124 and coupling an adjustment nut 163 to an upper end portion of the piston rod 161. Minimum applied pressure at which a relative movement starts to be generated between the moving block 120 and the coupling block 110 depending on the initial state of the spring 140 is mechanically set.

The load cell 170 has a bottom surface supported by the coupling block 110 and a measuring part which is directly in contact with the piston body 162, and receives the applied pressure from the spring 140. When the breast of the patient is photographed, a deformation no longer occurs after the deformation in which the breast of the patient is compressed to a predetermined degree occurs by the pressure pad 60 which is vertically moved. In this case, when the pressure pad driving part 70 continues to operate and the belt 74 presses down the moving block 120 in an arrow direction, a relative displacement occurs between the coupling block 110 and the moving block 120 while the spring 140 receiving repulsive force from the pressure pad 60 which is no longer descended by receiving the repulsive force from the breast of the patient is compressed. In other words, the spring 140 receiving the applied pressure from the pressure pad driving part 70 stores energy through an elastic deformation and transfers the applied pressure to the coupling block 110, and the load cell 170 provides the electrical signal by measuring the applied pressure in real time.

In addition, strong safety measures for protecting the patient may also be taken such as a relative movement range of the moving block 120 in a housing of the coupling block 110 being limited or the initial state of the spring 140 being adjusted by installing a support bolt 165 between the coupling block 110 and the moving block 120 as well as power supplied to the pressure pad driving part 70 being shut-down in the case in which the relative movement displacement exceeds a predetermined value by installing a safety switch 180 at a predetermined position, and the like. The reason that the safety switch 180 is operated depending on the relative movement displacement is that a strength of applied pressure applied to the breast of the patient becomes strong in proportion to the relative movement displacement between the coupling block 110 and the moving block 120 due to the existence of the spring 140 between the coupling block 110 and the moving block 120. The safety switch 180 may be installed at a position at which the moving block 120 arrives when the spring 140 is deformed as much as maximum applied pressure which may be applied to the patient is transferred. In addition, as the safety switch 180, a mechanical switch may be employed so that the patient may be protected under any situation.

Figure 6:
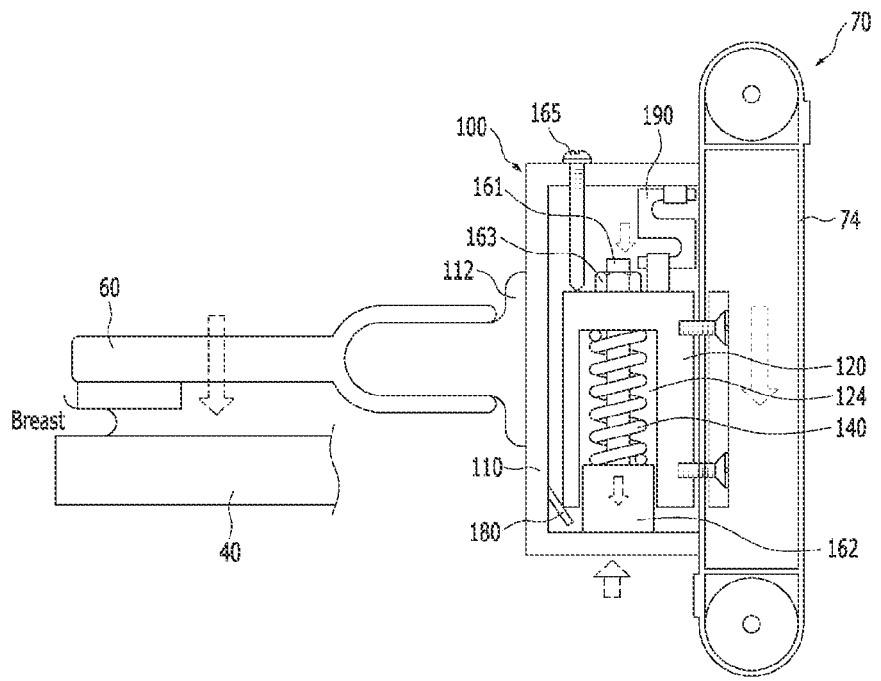
FIG. 6 is a schematic diagram showing a configuration of an applied pressure transferring part in a digital mammography device according to another exemplary embodiment of the present invention.

FIG. 6 is a schematic diagram showing a configuration of an applied pressure transferring part in a digital mammography device according to another exemplary embodiment of the present invention.

The configuration of the digital mammography device shown in FIG. 6 is substantially equal to that shown in FIG. 5, and only a difference therebetween will be described.

A tensile load cell 190 is installed between the coupling block 110 and the moving block 120 so as to be tensioned as the moving block 120 is relatively moved in the housing of the coupling block 110. Therefore, the piston body 162 is installed so that the bottom surface thereof is supported by the coupling block 110.

Similar to the load cell 170, the tensile load cell 190 provides an electrical signal by measuring tensile force generated according to the movement of the moving block 120 in real time.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A digital mammography device comprising:
   an X-ray generator to generate X-rays;
   an X-ray detector to receive generated X-rays passing through a subject;
   a pressure pad movably installed between the X-ray generator and the X-ray detector, to compress the subject;
   a pressure pad driving part including a motor and a power transferring part to move the pressure pad using power of the motor; and
   an applied pressure transferring part including a coupling block to which the pressure pad is fixed, and a moving block fixed to the power transferring part and movably connected to the coupling block, and configured to provide an electrical signal depending on a relative movement displacement between the coupling block and the moving block.

2. The digital mammography device according to claim 1, wherein the applied pressure transferring part further comprises:
   a spring disposed between the coupling block and the moving block and deformed depending on the relative movement displacement; and
   a load cell disposed at one end portion of the spring to provide the electrical signal according to a deformation of the spring.

3. The digital mammography device according to claim 2, further comprising a piston member installed between the one end portion of the spring and the load cell.

4. The digital mammography device according to claim 1, further comprising a controller to control the motor with the electrical signal.

5. The digital mammography device according to claim 4, further comprising a safety switch to control the motor when the relative movement displacement exceeds a preset range.

6. The digital mammography device according to claim 1, further comprising a safety switch to control the motor when the relative movement displacement exceeds a preset range.

7. An X-ray imaging device comprising:
   an X-ray generator to generate X-rays;
   an X-ray detector to receive the generated X-rays passing through a subject;
   a pressure pad movably installed between the X-ray generator and the X-ray detector, the pressure pad is configured to compress the subject;
   a pressure pad driving part including a motor and a power transferring part to move the pressure pad using power of the motor; and
   an applied pressure transferring part including a coupling block to which the pressure pad is fixed and a moving block fixed to the power transferring part and relatively and movably connected to the coupling block, wherein the applied pressure transferring part is configured to provide an electrical signal depending on a relative movement displacement between the coupling block and the moving block.

* * * * *